United States Patent [19]

O'Connell

[11] Patent Number: 5,678,555
[45] Date of Patent: Oct. 21, 1997

[54] METHOD OF LOCATING AND MARKING VEINS

[76] Inventor: Peter O'Connell, 4319 Market St., Boardman, Ohio 44512

[21] Appl. No.: 629,021

[22] Filed: Apr. 8, 1996

[51] Int. Cl.⁶ ..................................................... A61B 6/00
[52] U.S. Cl. ......................................................... 128/664
[58] Field of Search .................................. 128/664, 665, 128/736; 374/121, 124, 129

[56] References Cited

U.S. PATENT DOCUMENTS

| | | |
|---|---|---|
| 4,887,606 | 12/1989 | Yock . |
| 4,945,239 | 7/1990 | Wist et al. ............................. 128/664 |
| 5,080,103 | 1/1992 | Olivier . |
| 5,131,395 | 7/1992 | Gehlbach . |
| 5,309,915 | 5/1994 | Ember . |
| 5,313,951 | 5/1994 | Zhao ....................................... 128/664 |

*Primary Examiner*—Marvin M. Lateef
*Assistant Examiner*—Derrick Fields
*Attorney, Agent, or Firm*—Harpman & Harpman

[57] ABSTRACT

A method for locating blood vessels in a live human body utilizing infrared scanning and imaging techniques to distinguish relative temperature differences between blood carrying vessels and surrounding human tissue. An infrared imaging camera is used to detect the emissions of an object to differentiate the specific elevated surface temperature associated with blood vessels in a human body and surrounding tissue and marking same by the introduction of a marking device visible through temperature differentiation within the infrared imaging field.

3 Claims, 1 Drawing Sheet

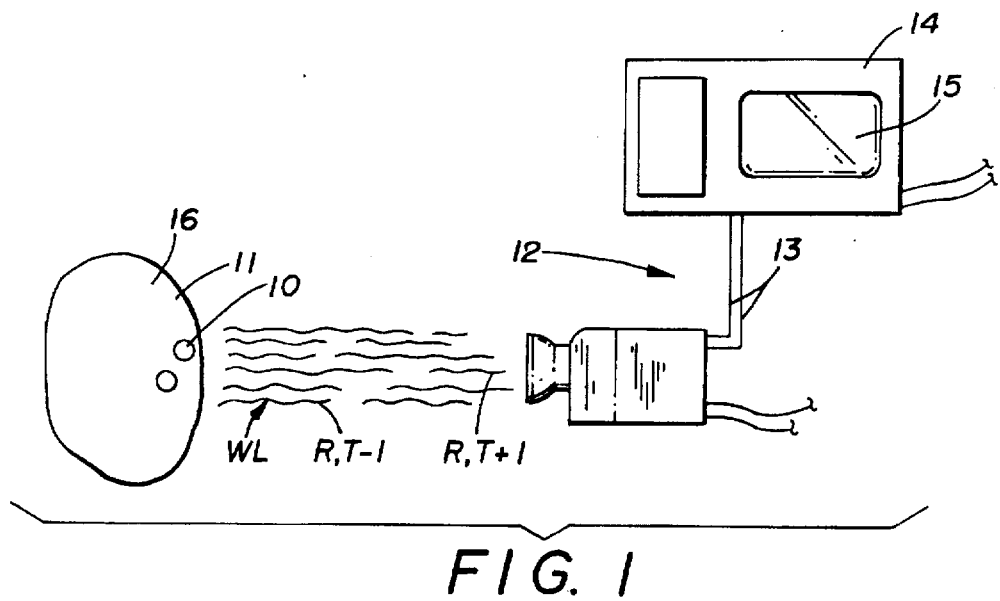
FIG. 1
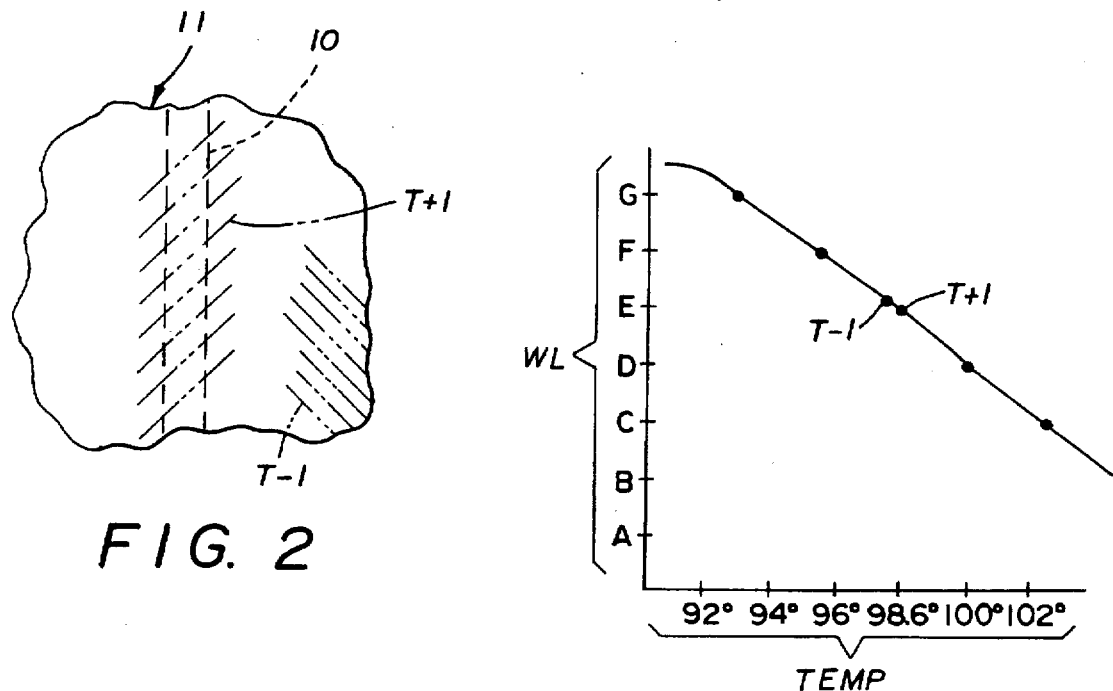
FIG. 2
FIG. 3
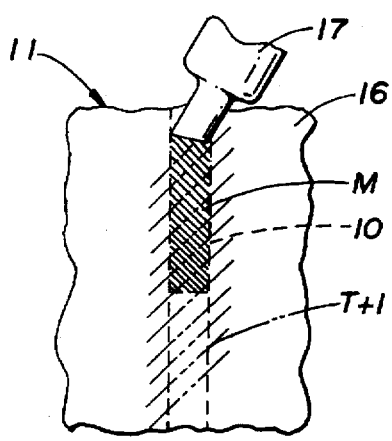
FIG. 4

METHOD OF LOCATING AND MARKING VEINS

BACKGROUND OF THE INVENTION

1. Technical Field

This invention relates to an improved method for locating and marking blood carrying vessels (veins) in a live human in a non-invasive application using remote detection source.

2. Description of Prior Art

Prior art devices and methods for locating blood carrying veins in a human body have been directed to physical and visual observation of the veins by experienced medical personnel for the insertion of blood drawing needles and IV's used to collect blood and/or to administer medications or other acquiesce based solutions associated with medical care of the patient.

Non-invasive means and method have heretofore been based upon the generation of ultra-sonic signals and detection of their return echos (using the doppler effect) to penetrate the human body with sound waves and determine by return echo the location of pulsating flow of blood through a vein, see for example U.S. Pat. Nos. 5,309,915, 5,131,395, 5,080,103 and 4,887,606.

In U.S. Pat. No. 5,309,915 an apparatus for locating blood vessels is disclosed having a self-contained compact ultrasonic signal generator that transmits and receives ultra-sonic signals directed towards the patient selectively determining by the differential of signal return the relative position of the vein.

U.S. Pat. No. 5,131,395 is directed towards an ultra-sonic apparatus for guiding needles to surface vessels in which an ultra-sonic transmitter and receiver is positioned on the adjacent end of a needle and is used to transmit and receive high energy ultra-sonic signals to determine the relative position of surface veins.

In U.S. Pat. No. 5,080,103 a syringe for doppler sonographically aided penetration is disclosed in which a syringe becomes the transmitter and receiver of ultra-sonic sound waves in order to determine and locate the relative position of the vein as the syringe is positioned above the surface of a patient.

Finally, U.S. Pat. No. 4,887,606 is directed to an apparatus for use in cannulation of blood vessels in which a hollow needle is utilized having a transducer mounted on one end positioned within for transmitting and receiving ultra-sonic waves through the sharpened end of the needle.

SUMMARY OF THE INVENTION

A non-invasive method for detection and location of blood carrying veins by using the temperature differential between the blood carrying veins and the surrounding body tissue, by the use of infrared pyronetues the temperature on any point of a target surface can be measured without direct contact with the target surface. The location of the temperature differential associated with blood carrying veins on a live human patient can be determined and visually illustrated by use of a focal plane array infrared camera with a selective electronic output to a internal or remote viewing screen.

DESCRIPTION OF THE DRAWINGS

FIG. 1 is a graphic illustration of the present invention displaying a human limb and associated blood carrying veins and a representation of an infrared scanning equipment and output screen;

FIG. 2 is an enlarged graphic illustration denoting temperature differential of blood carrying veins and surrounding tissue achieved by the present invention;

FIG. 3 is a graph illustrating temperature to infrared wave length association; and FIG. 4 is a graphic illustration of marking a located blood carrying vessel by infrared radiation detection of temperature differential using a visually apparent marking instrument.

DESCRIPTION OF THE PREFERRED EMBODIMENT

A method of detecting and visually marking blood vessels 10 in a live human being 11 using an infrared imaging camera and processor system 12. An infrared radiation R as indicated in FIG. 1 of the drawings is classified as part of the electro-magnetic spectrum from ˜0.75 um to >1,000 microns where the radiation becomes indistinguishable from microwaves at the high end of the radio spectrum.

Infrared radiation R is subject to the basic laws of reflection, refraction, polarization and defraction in the same manner as that of visible light waves.

Infrared radiation R wave length L changes as the temperature T of the object heats up. Wherein cool target radiation is predominately in the long wave length area as best seen in FIG. 3 of the drawings. When an object becomes hotter, the infrared radiation wave lengths become shorter thus infrared scanning equipment can differentiate between relative temperatures of objects and surface areas by interpreting the long and short wave length of the infrared emission therefrom.

The instant invention utilizes the infrared imaging camera and processing system 12 utilizing a focal plane array infrared camera such as model 812, manufactured by FLIR Systems of Portland, Oreg. having a spectral range of 8–12 um which corresponds to an effective temperature determining range of −20 degrees to 500 degrees centigrade with a minimum discernable temperature of 0.06 degrees centigrade to 30 degrees centigrade which is well within the blood carrying vein 10 temperature difference between surrounding tissue and the vein.

The infrared imaging camera system 12, chosen for illustration, produces real time infrared thermal images/analysis capable of discerning the relative temperature difference (T+1) between the blood carrying vessel 10, best seen in FIG. 2 of the drawings, and the surrounding surface area 13 delineated by temperature (T−1). The temperature difference is visually displayed on a processor 14 view screen 15 interconnected to the infrared imaging camera of the system 12 by cables 16.

The present process of the invention utilizes multiple steps to determine and mark vein location defined by first; positioning and patient's arm 16 (in this example) to be scanned before the infrared scanning camera system 12.

Activating the infrared camera scanning system 12 and connected imaging processor.

Defining a target area on the arm 16 for infrared emission identification.

Determining the position of the blood carrying vessel 10 by an infrared image that illustrates the elevated temperature associated with blood carrying vein 10 to the surrounding area.

Introducing a marking element 17 onto the target area as best seen in FIG. 4 of the drawings and marking the vein location with a visually discernable mark, illustrated by diagonal lines M.

Once the vein 10 has been located and visually marked, the method of the invention is completed.

Given the fact that emissivity of infrared radiation from an object is affected by other factors such as surface texture, surface treatment and angle of observation i.e. (radiation angle) it will be necessary to maintain established location parameters for each patient involving the distance and viewing angle of the infrared camera system 12 from the target and adjusting for unusual skin texture or skin color to obtain constant and reliable results.

The method of this invention is particularly useful in situations where veins are difficult to locate visually by palpitation and in situations where a vein must be located rapidly. Because the device is non-invasive and is accurate, the patient will undergo considerably less pain and trauma. Trained medical personnel associated with utilization of the method of this invention will be able to distinguish and appropriately mark blood carrying veins with practice utilizing the real time display illustrating the relative temperature differentials between the surrounding body tissue and the blood carrying vein 10 and the associated introduction of a much cooler marking instrument to achieve precise location and visual marking of same as hereinbefore described.

It will thus be seen that the above referred to method has been illustrated and described and it will be apparent to those skilled in the art that various changes and modifications may be made therein without departing from the spirit of the invention, therefore

I claim:

1. A method of locating and marking blood vessels in a live human patient utilizing infrared radiation emissions comprising; providing an infrared imaging camera and processor, providing a live human to be scanned by the infrared imaging camera, detecting a selected target area on the human to be scanned, determining relative temperature difference on the surface of the patient between the blood carrying vessel and associated human tissue by detecting discernible infrared wave length radiation from said live human, providing a location marking device to be introduced into the target area to mark the located blood vessel on the surface of said patient.

2. The method of locating and marking blood carrying veins set forth in claim 1 wherein said location marker device provides a temporary visible mark on the patient associated with the exact location of said blood carrying vessels.

3. The method of locating and marking blood carrying vessels in a live patient set forth in claim 1 wherein said imaging camera and processor has an effective temperature range between −20 degrees centigrade to 500 degrees centigrade, a minimum discernable temperature of 0.06 degrees centigrade to 30 degrees centigrade, a spectral range of 8–12 microns and a source of power and view screen associated therewith.

* * * * *